(12) United States Patent
Merschon et al.

(10) Patent No.: US 9,460,563 B2
(45) Date of Patent: Oct. 4, 2016

(54) DIFFERENTIAL MAPPING OF A BODY ORGAN

(71) Applicant: BIOSENSE WEBSTER (ISRAEL) LTD., Yokneam (IL)

(72) Inventors: Asaf Merschon, Karkur (IL); Fady Massarwa, Baka el Gharbiya (IL); Liav Moshe Adi, Haifa (IL); Eliahu Zino, Atlit (IL); Gil Zigelman, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 5 days.

(21) Appl. No.: 14/555,985

(22) Filed: Nov. 28, 2014

(65) Prior Publication Data

US 2016/0155274 A1    Jun. 2, 2016

(51) Int. Cl.
*G06T 15/00* (2011.01)
*G06T 19/20* (2011.01)
*A61B 5/00* (2006.01)
*G06T 7/00* (2006.01)

(52) U.S. Cl.
CPC ............... *G06T 19/20* (2013.01); *A61B 5/743* (2013.01); *G06T 7/0012* (2013.01); *G06T 7/0081* (2013.01); *G06T 2207/20021* (2013.01); *G06T 2207/30048* (2013.01); *G06T 2210/41* (2013.01); *G06T 2210/62* (2013.01); *G06T 2219/004* (2013.01); *G06T 2219/2012* (2013.01)

(58) Field of Classification Search
CPC ... G06T 17/05; G06T 17/0026; G06T 15/08; G01V 1/30; A61B 5/415; A61B 19/22; A61B 8/065
USPC ......... 345/419, 420, 424; 382/128; 600/441, 600/459
See application file for complete search history.

(56) References Cited

U.S. PATENT DOCUMENTS

| | | | | |
|---|---|---|---|---|
| 6,765,570 B1 * | 7/2004 | Cheung | ............ | G06T 17/05 345/420 |
| 7,248,258 B2 * | 7/2007 | Acosta | ............ | G06T 15/08 345/419 |
| 7,697,373 B1 * | 4/2010 | Padgett | ............ | G01V 1/30 367/38 |
| 7,991,600 B2 * | 8/2011 | Callegari | ............ | G01V 1/30 345/424 |
| 8,335,552 B2 * | 12/2012 | Stiles | ............ | A61B 5/415 382/128 |
| 8,686,996 B2 * | 4/2014 | Cheung | ............ | G06T 17/05 345/420 |
| 8,731,875 B2 * | 5/2014 | Hilliard | ............ | G06T 17/05 703/1 |
| 8,797,319 B2 * | 8/2014 | Lin | ............ | G06T 15/08 345/419 |
| 9,011,340 B2 * | 4/2015 | Tal | ............ | G06T 7/0026 600/459 |
| 9,033,887 B2 * | 5/2015 | Ionasec | ............ | A61B 8/065 600/441 |
| 9,101,397 B2 * | 8/2015 | Guthart | ............ | A61B 19/22 |
| 9,171,391 B2 * | 10/2015 | Smith | ............ | G06T 13/20 |
| 9,232,984 B2 * | 1/2016 | Guthart | ............ | A61B 19/22 |
| 2014/0100442 A1 | 4/2014 | Begin et al. | | |

FOREIGN PATENT DOCUMENTS

| | | | |
|---|---|---|---|
| EP | 2064991 A2 | 6/2009 | |
| EP | 2485194 A2 | 8/2012 | |
| EP | 2638853 A1 | 9/2013 | |

OTHER PUBLICATIONS

EP 15 19 6783—Extended EP Search Report dated Mar. 29, 2016.

*Primary Examiner* — Phu K Nguyen

* cited by examiner

(74) *Attorney, Agent, or Firm* — Louis J. Capezzuto

(57) ABSTRACT

A method for mapping a body organ, including receiving a three-dimensional (3D) map of the body organ having a multiplicity of map elements, each map element having a graphic attribute indicative of a local property of the body organ. The method further includes delineating a selected region of the map, so that the map is divided into the selected region and a non-selected region. The 3D map is displayed while the graphic attribute of the map elements specifically within the selected region are altered.

22 Claims, 9 Drawing Sheets

DIFFERENTIAL MAPPING OF A BODY ORGAN

FIELD OF THE INVENTION

The present invention relates generally to graphic displays, and specifically to displaying of electrophysiological data of a body organ in a map.

BACKGROUND OF THE INVENTION

In medical procedures, such as mapping the electrical activity of the heart, there is typically a large amount of information that may be presented to a professional performing the mapping, and/or performing a procedure using the mapping. The large amount of information presented may lead to difficulties in comprehension of the information.

SUMMARY OF THE INVENTION

An embodiment of the present invention provides a method for mapping a body organ, including:

receiving a three-dimensional (3D) map of the body organ having a multiplicity of map elements, each map element having a graphic attribute indicative of a local property of the body organ;

delineating a selected region of the map, so that the map is divided into the selected region and a non-selected region; and displaying the 3D map while altering the graphic attribute of the map elements specifically within the selected region.

Typically, displaying the 3D map includes not altering the graphic attribute of the geometric map-elements within the non-selected region.

In a disclosed embodiment delineating the selected region includes generating a closed perimeter on the 3D map separating the selected region from the non-selected region. The selected region may be within the perimeter. Alternatively, the selected region may be external to the perimeter.

In a further disclosed embodiment delineating the selected region includes initially generating a closed perimeter on the 3D map separating the selected region from the non-selected region, and subsequently changing the closed perimeter so as to alter the selected region and the non-selected region.

In a yet further disclosed embodiment the body organ includes a heart, and the local property includes at least one of a temperature, an electropotential, a resistivity, a contractility, and a local activation time (LAT) of the heart.

In an alternative embodiment the method also includes:

incorporating into the 3D map one or more geometric figures, each geometric figure being representative of at least a portion of an entity associated with a local region of the body organ and having a further graphic attribute, and displaying the 3D map while altering the further graphic attribute of the one or more geometric figures specifically within the selected region.

In a further alternative embodiment the graphic attribute includes at least one of a color value, a visibility, and a transparency.

There is further provided, according to an embodiment of the present invention, a method for mapping a body organ, including:

receiving a three-dimensional (3D) map of the body organ including one or more geometric figures, each geometric figure having a graphic attribute and being representative of at least a portion of an entity associated with a local region of the body organ;

delineating a selected region of the map, so that the map is divided into the selected region and a non-selected region; and displaying the 3D map while altering the graphic attribute of the each geometric figure specifically within the selected region.

The geometric figures may include at least one of a distal tip icon representative of a location and orientation of a catheter distal tip and an ablation icon representative of an ablation performed on a region of the body organ.

There is further provided, according to an embodiment of the present invention, apparatus for mapping a body organ, including:

a processor which is configured to receive a three-dimensional (3D) map of the body organ having a multiplicity of map elements, each map element having a graphic attribute indicative of a local property of the body organ, and to delineate a selected region of the map, so that the map is divided into the selected region and a non-selected region; and a screen which is configured to display the 3D map while altering the graphic attribute of the map elements specifically within the selected region.

There is further provided, according to an embodiment of the present invention, apparatus for mapping a body organ, including:

a processor which is configured to receive a three-dimensional (3D) map of the body organ including one or more geometric figures, each geometric figure having a graphic attribute and being representative of at least a portion of an entity associated with a local region of the body organ, and to delineate a selected region of the map, so that the map is divided into the selected region and a non-selected region; and a screen which is configured to display the 3D map while altering the graphic attribute of the each geometric figure specifically within the selected region.

The present disclosure will be more fully understood from the following detailed description of the embodiments thereof, taken together with the drawings, in which:

DETAILED DESCRIPTION OF EMBODIMENTS

Overview

Embodiments of the present invention provide a system for reducing the amount of visual information presented to a user of the system, who is typically a medical professional performing a surgical procedure. The visual information is presented to the user on a screen which displays a three-dimensional (3D) map of a body organ, herein by way of example assumed to be the heart of a patient undergoing the procedure. The 3D map is formed of a multiplicity of map elements, and each map element has a graphic attribute, such as a color value, that is associated with the element and that is indicative of a local property of the heart, such as a unipolar or bipolar local activation time (LAT). The graphic attribute of a map element defines how the map element is displayed to the user of the system.

A closed perimeter may be delineated on the map, typically by using a pointing device. The perimeter divides the map into two regions, one within the perimeter and the other external to the perimeter. One of these regions is assumed to be a selected region, the other region being a non-selected region. The map is displayed on the screen while the graphic attributes of the map elements within the selected region are altered, the graphic attributes of the elements in the non-selected region being unaltered.

The alteration of the graphic attributes within one of the delineated regions is typically so as to reduce the amount of visual information presented in the region. The reduction enhances the ability of the user to concentrate on the information provided by the graphic attributes of the elements in the other region, and mitigates "visual overload."

System Description

Figure 1:
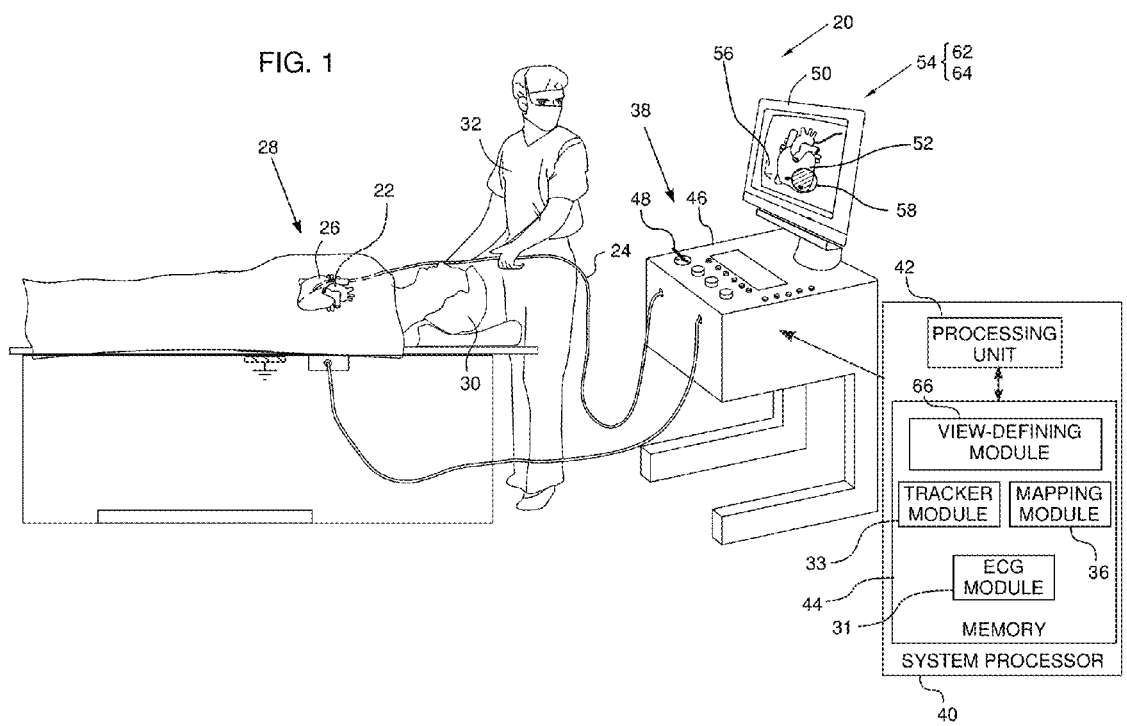
FIG. 1 is a schematic illustration of a view-defining system, according to an embodiment of the present invention.

Reference is now made to FIG. 1, which is a schematic illustration of a view-defining system 20, according to an embodiment of the present invention. System 20 is typically used during a medical procedure on a body organ, and may be configured to define different views of substantially any mapped physiological parameter or combinations of such parameters of the organ. In the description herein the body organ, by way of example, is assumed to comprise the heart, and an example of a mapped parameter may comprise a local activation time (LAT) derived from intra-cardiac electrocardiogram (ECG) potential-time relationships. (The measurement and use of LATs are well known in the electrophysiological arts.) However, in the case of the body organ comprising the heart, system 20 may define views using other mapped physiological parameters, such as the location and/or size of cardiac lesions generated by ablation of the heart, the force applied to a region of the heart wall by a catheter, and the temperature of the heart wall region.

The following description, except where otherwise stated, assumes that system 20 senses electrical signals from a heart 22, using a probe 24. A distal end 26 of the probe is assumed to have an electrode 28 for sensing the signals. Typically, probe 24 comprises a catheter which is inserted into the body of a subject 30 during a cardiac procedure performed by a user 32 of system 20. In the description herein user 32 is assumed to be a medical professional.

System 20 may be controlled by a system processor 40, comprising a processing unit 42 communicating with a memory 44. Processor 40 is typically mounted in a console 46, which comprises operating controls 38 which include a pointing device 48 such as a mouse or trackball. Professional 32 uses device 48 to interact with the processor, which, as described below, may be used to define the view presented by system 20 to the professional on a screen 50.

The screen displays a three-dimensional (3D) map 52 of the internal surface of heart 22, together with items of auxiliary information 54 related to the heart and/or the procedure. The items of auxiliary information are superimposed on the map, so that each displayed map element incorporating the information, typically a group of pixels displayed on screen 50, has a corresponding graphic attribute.

Herein, the items of auxiliary information are divided into two categories: a first category 62, also termed property parameters 62, that typically represent local characteristics or properties of the heart surface; and a second category 64, also termed geometric FIG. 64, that typically represent elements involved with the procedure being performed on the heart, or that graphically depict information associated with a local region of the heart. Examples of the two categories are provided below.

Map 52 is plotted on a set of three orthogonal axes defining a frame of reference for the map, and a representation 56 of the axes may be displayed on screen 50.

Property parameters 62 typically include local characteristics of the surface itself, such as a temperature, an electropotential, a resistivity, or a contractility of the surface, as well as combinations and derivatives of these parameters such as a local activation time (LAT) derived from a local change of surface electropotential with time.

Geometric FIG. 64 typically include geometric graphic elements representing items physically separate from the heart surface represented by map 52, or items providing information about the heart surface. For example, FIG. 64 may include an icon indicative of a location and orientation of distal tip 26 with respect to the internal surface of the heart. FIG. 64 may also include other icons indicative of other probe distal tips physically separate from the heart surface. Other related figures that may be superimposed on the map include an icon representing an ablation site, and/or parameters of the ablation site. FIG. 64 may also include one or more cursors having positions on screen 50 that are controlled by pointing device 48.

As stated above geometric FIG. 64 may include elements involved in the procedure being performed, such as a fluoroscope background image, an ultrasound image, an indication of the force on a catheter, and/or an indication of an ablation location. The latter may include information about the ablation such as the power used, and/or an overall energy applied, for the ablation.

Processor 40 uses software, including a probe tracker module 33 and an ECG module 31, stored in memory 44, to operate system 20. The software may be downloaded to processor 40 in electronic form, over a network, for example, or it may, alternatively or additionally, be provided and/or stored on non-transitory tangible media, such as magnetic, optical, or electronic memory.

ECG module 31 is coupled to receive electrical signals from electrode 22. The module is configured to analyze the signals and may present the results of the analysis in a standard ECG format, typically a graphical representation moving with time, on screen 48. Alternatively or additionally, the results may be incorporated into map 52, for example as values of LATs derived from the electrical signals.

Probe tracker module 33 tracks sections of probe 24 while the probe is within subject 30. The tracker module typically tracks both the location and orientation of distal end 26 of probe 24, within the heart of subject 26. In some embodiments module 33 tracks other sections of the probe. The tracker module may use any method for tracking probes known in the art. For example, module 33 may operate magnetic field transmitters in the vicinity of the subject, so that magnetic fields from the transmitters interact with tracking coils located in sections of the probe being tracked. The coils interacting with the magnetic fields generate signals which are transmitted to the module, and the module analyzes the signals to determine a location and orientation of the coils. (For simplicity such coils and transmitters are not shown in FIG. 1.) The Carto® system produced by Biosense Webster, of Diamond Bar, Calif., uses such a tracking method.

Alternatively or additionally, tracker module 33 may track probe 24 by measuring impedances between electrode 22 and electrodes on the skin of subject 30. (In this case electrode 22 may provide both ECG and tracking signals.) The Carto3® system produced by Biosense Webster uses both magnetic field transmitters and impedance measurements for tracking.

Using tracker module 33, processor 40 is able to measure locations of distal end 26, and form location coordinates of the locations in the frame of reference of map 52 referred to above. The location coordinates are assumed to be stored in a mapping module 36. In addition, mapping module 36 is assumed to store location coordinates of items of auxiliary information 54 associated with heart 22.

Map 52 and items 54 typically present a large amount of visual information to user 32, and the large amount of information may lead to the user experiencing "visual overload." Embodiments of the present invention enable the user to selectively reduce the overall amount of information presented, and thus mitigate or remove any such overload. In order to implement such a reduction, user 32 is able to define a region 58 of map 52, using a view-defining module 66 installed in memory 44, which will appear differently to the user than the remainder of the map.

Figure 2:
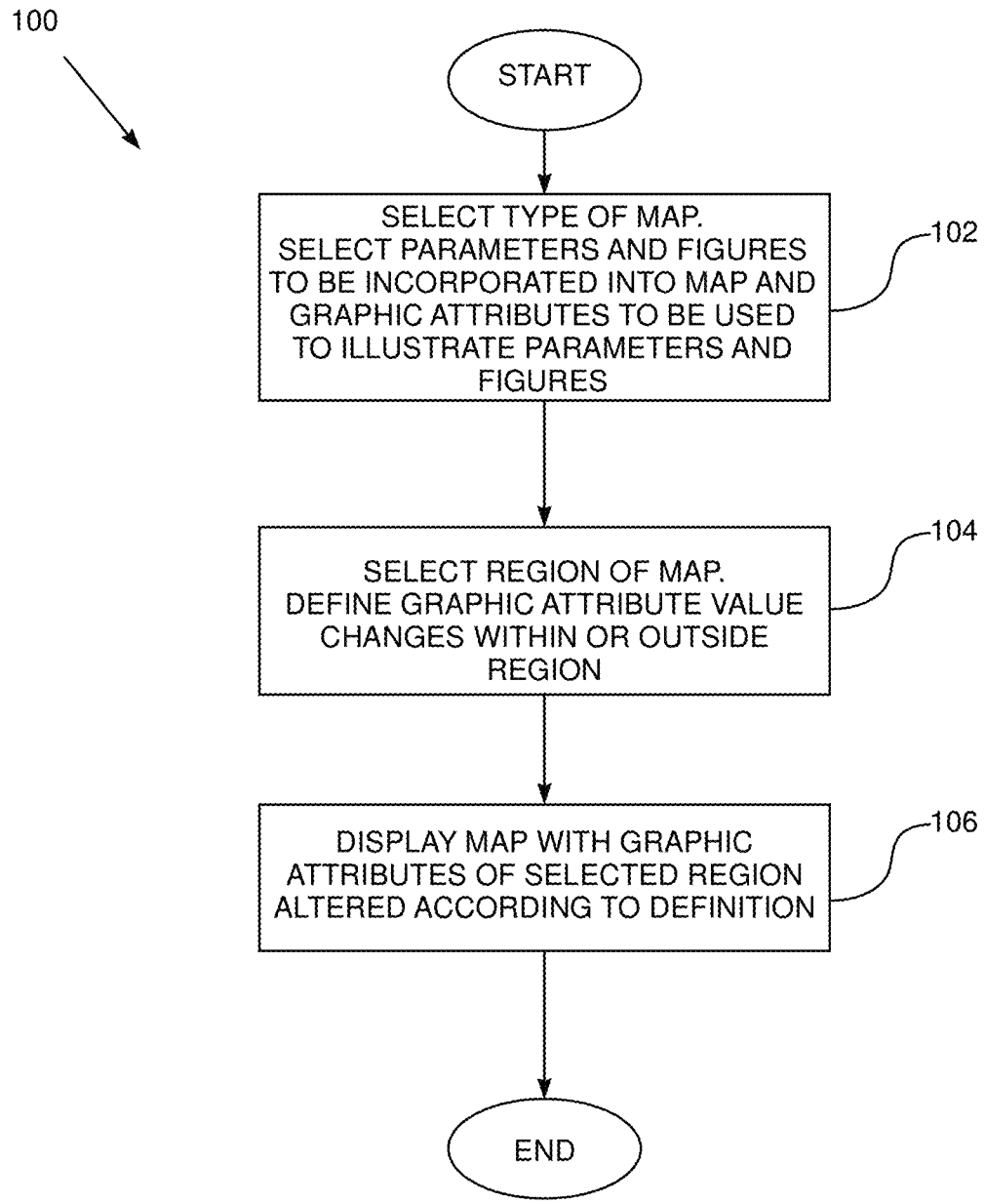
FIG. 2 is a flowchart of a process used by a user of the system of FIG. 1 to define a region, according to an embodiment of the present invention.
Figure 3:
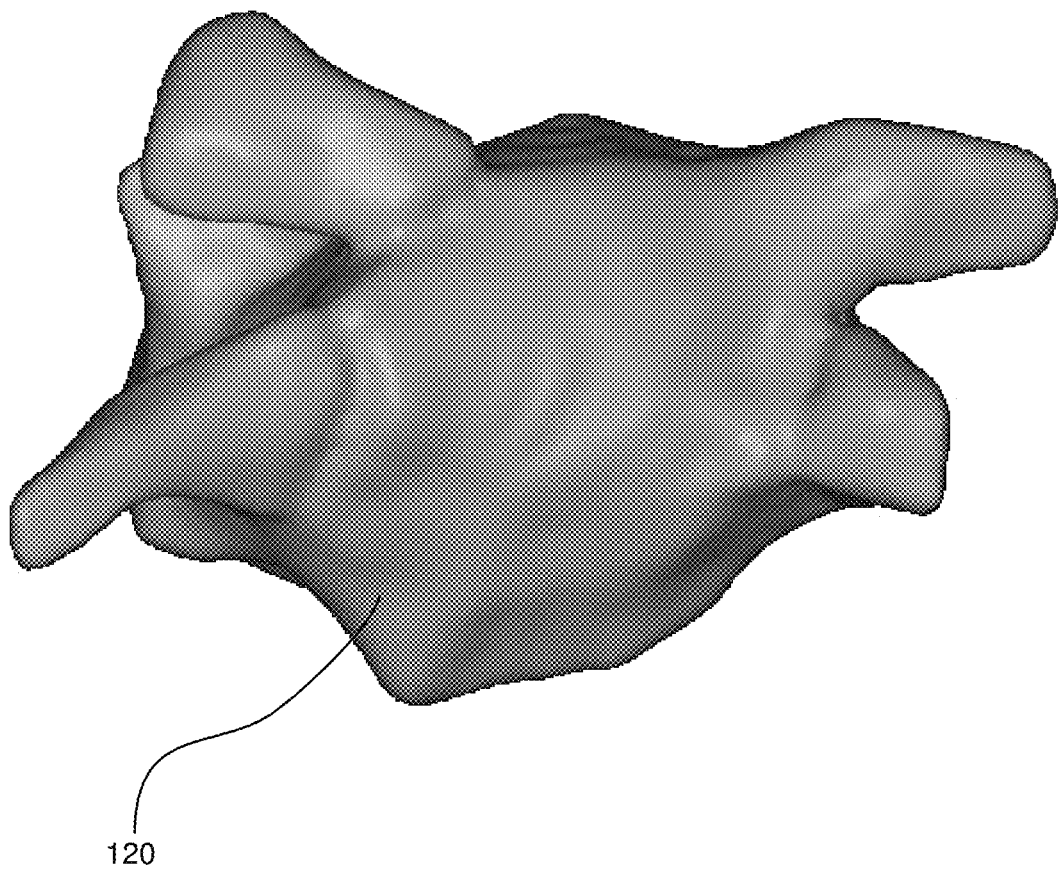
FIG. 3 is a schematic illustration of a surface map of a chamber of a heart, according to an embodiment of the present invention.
Figure 4:
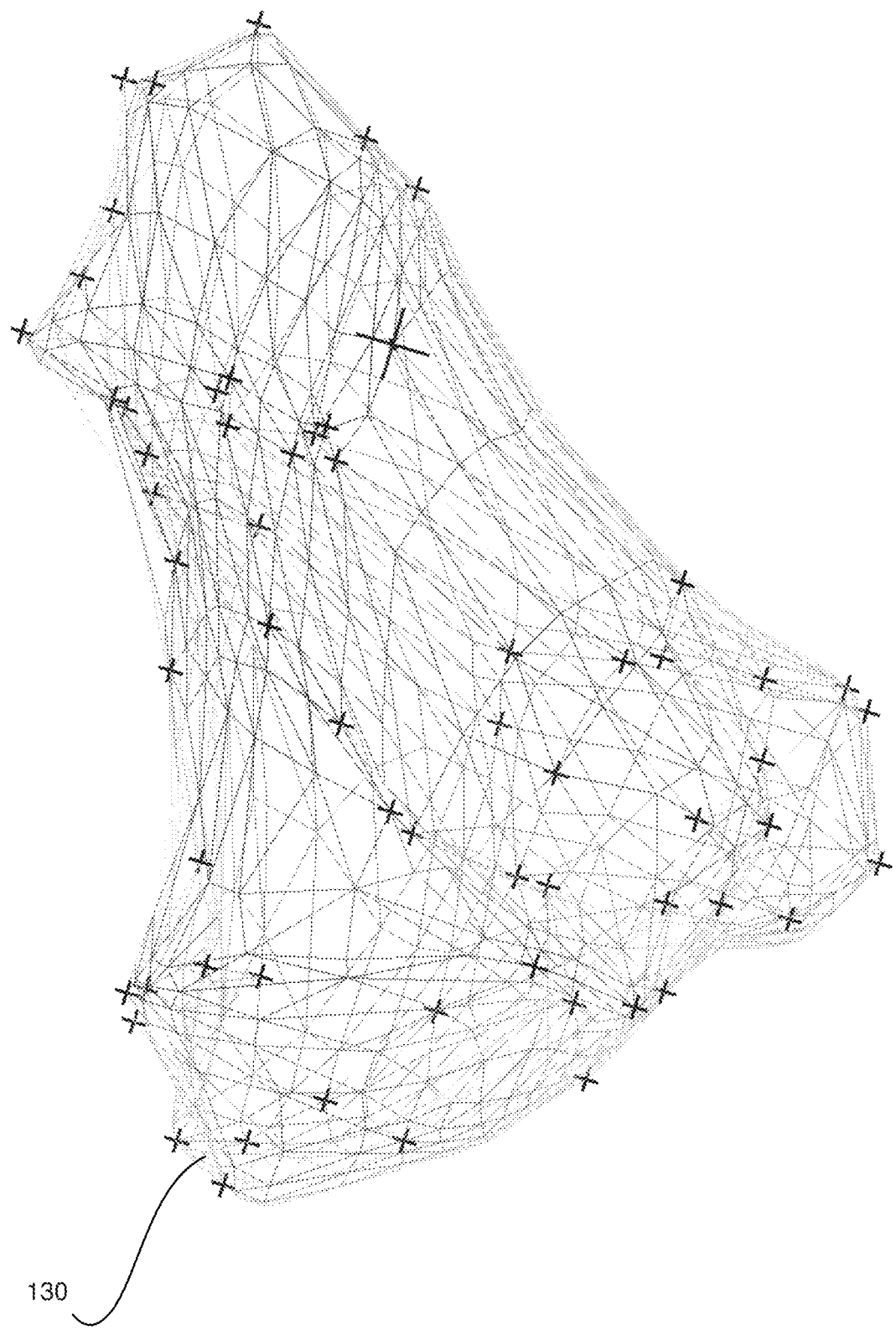
FIG. 4 is a schematic illustration of a mesh map of a chamber of a heart, according to an embodiment of the present invention.

FIG. 2 is a flowchart 100 of a process used by user 32 to define region 58, and FIGS. 3-9 are schematic diagrams illustrating the steps, according to embodiments of the present invention. In an initial step 102, the user selects the type of three-dimensional (3D) map of the body organ, herein assumed to be heart 22, to be displayed. Typical types of maps which may be selected include a surface 120 plotting the topography of a chamber of the heart, such as is illustrated in FIG. 3, or a mesh 130 plotting the topography, such as is illustrated in FIG. 4. (A surface such as that illustrated in FIG. 3 is typically generated from a mesh.) The selected map may also comprise a combination of maps. In some embodiments, the map may comprise one or more background images, such as a fluoroscope, an ultrasound, an MRI (magnetic resonance imaging), and/or a computerized tomography (CT) image. For simplicity and clarity, the following description assumes that the selected map comprises a mesh or a surface, and those having ordinary skill in the art will be able to adapt the description, mutatis mutandis, for other types of image.

The user selects one or more property parameters 62 of the heart that are to be incorporated into the map. Examples of property parameters 62 are described above, and by way of example, in the following description, a local activation time (LAT), derived from the change of surface electropotential with time, is assumed to be a property parameter 62 incorporated into the selected map.

In addition, in the initial step, the user may select one or more geometric FIG. 64 (described above) to be incorporated into the selected map. By way of example, an icon representing the location and orientation of distal tip 26 is assumed to be a structure 64 illustrated on the selected map.

Each of the selections is illustrated by applying preselected graphic attributes to map elements representative of the selection. Thus, for the case of the LAT property parameter being incorporated into a surface such as FIG. 3, different colors may be applied to regions of the surface, a given color representing a specific value of an LAT. Consequently, for each pixel of the surface there is a specific RGB (red/green/blue) set of values that corresponds to the LAT value. In the case of a mesh such as FIG. 4, the different RGB values of the LAT property parameter may be applied to each line and/or vertex of the mesh.

In the case of the icon geometric figure being incorporated into the surface or into the mesh, a distinctive shape may be used, and typically specific colors and/or patterns are applied to the shape.

In the figures of the present disclosure different colors, for example providing the additional information referred to above, are schematically shown as different types of lines and vertices for the map when it is in the form of a mesh, and as different grayscale levels for the map when it is in the form of a surface. In the case of the presentation of the actual map on screen 50, a legend for interpretation of the different colors is typically presented on the screen.

Figure 5:
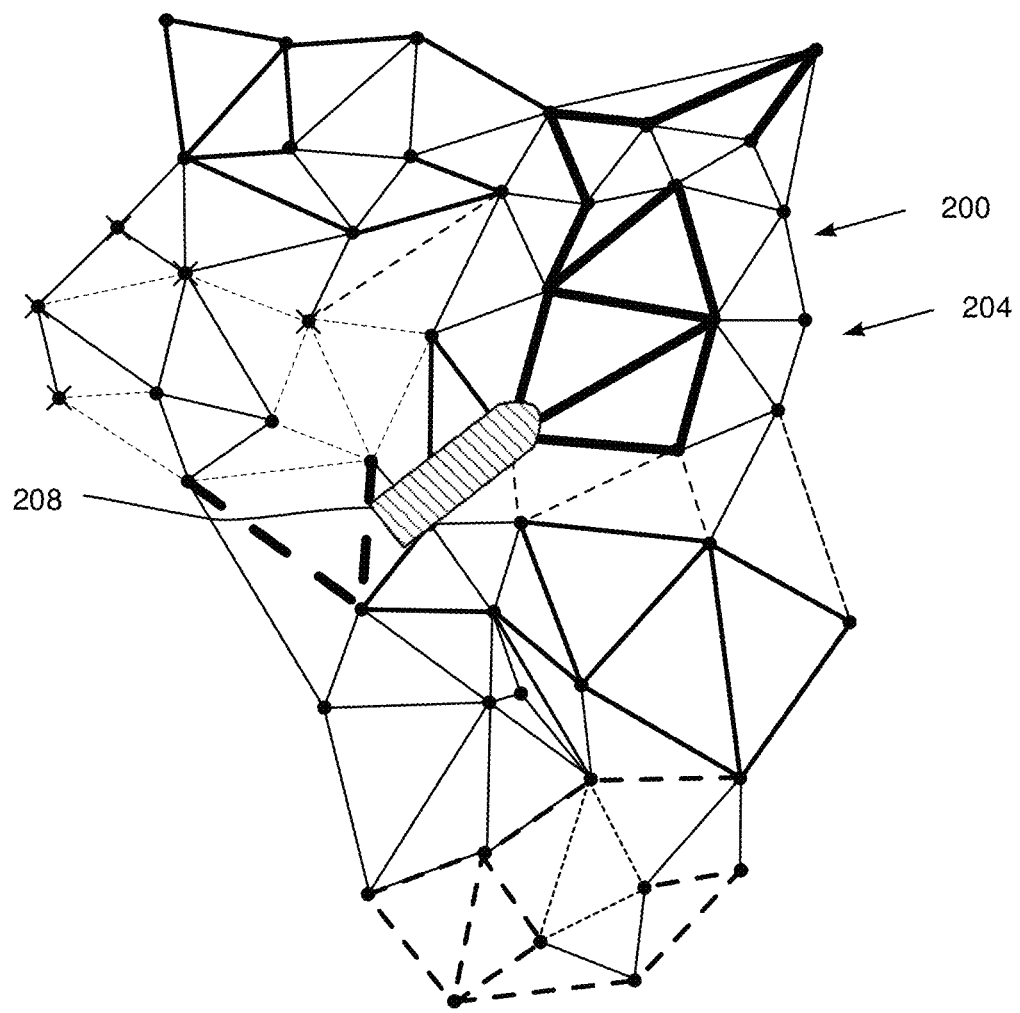
FIG. 5 is a schematic diagram of a mesh map assumed to be selected by the user of the system of FIG. 1, according to an embodiment of the present invention.

FIG. 5 is a schematic diagram of a mesh map 200 assumed to be selected by the user in the initial step, according to an embodiment of the present invention. Map 200 is assumed to have values of LATs 204 incorporated into the map as a property parameter 62, the LAT values being indicated on screen 52 by different colors, with a legend 206 translating between the colors and the values being displayed on the screen. In the figure the different colors of the LATs are indicated by different types of lines, also shown in legend 206. Map 200 also has an icon 208, representative of a location and orientation of distal tip 26 within the region represented by the map, incorporated into the map as a geometric FIG. 64. Icon 208 is by way of example shaped as cylinder with a rounded end, and typically is colored so as to be easily distinguishable from the colors used for the LAT values. The coloration of icon 208 is illustrated in the figure by hatching.

Figure 6:
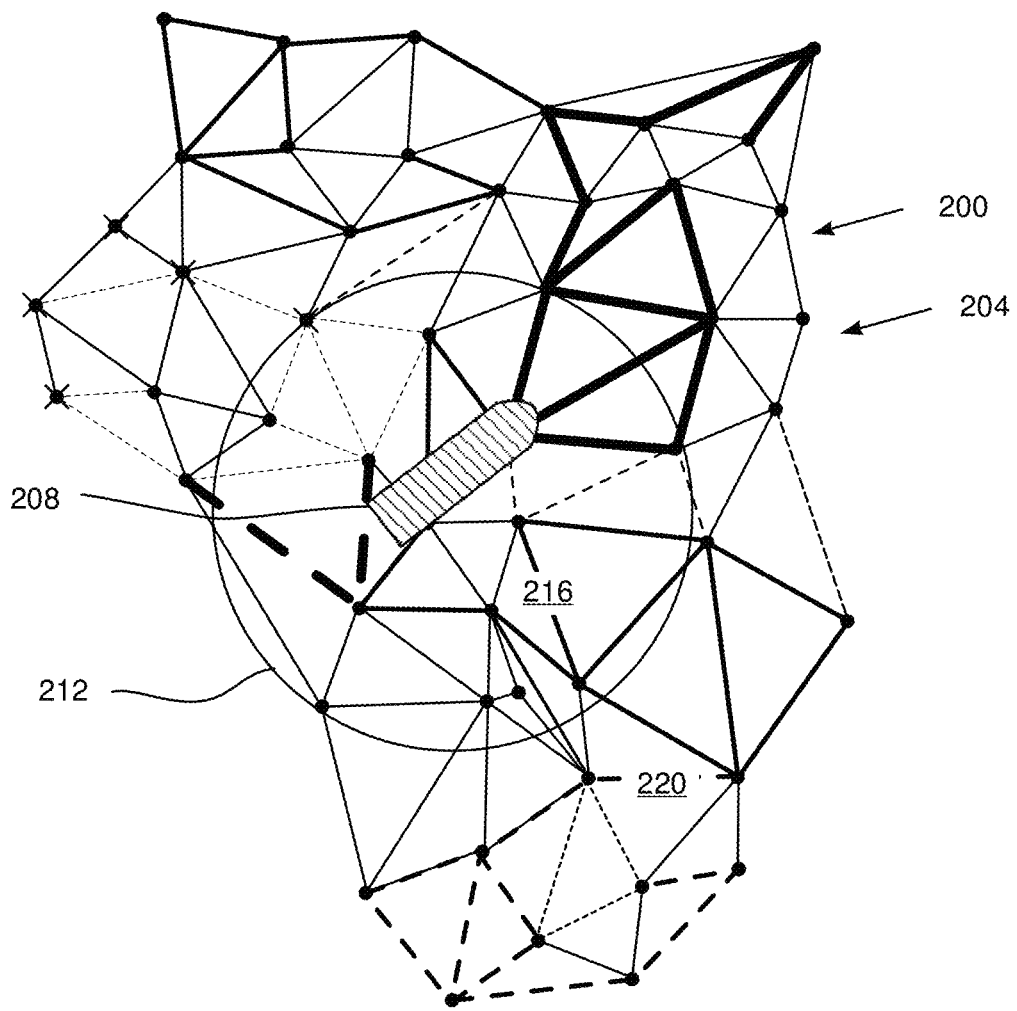
FIG. 6 is a schematic diagram of the mesh map of FIG. 5 with a delineated perimeter, according to an embodiment of the present invention.

In a selection step 104, illustrated by FIG. 6, the user delineates a closed perimeter 212 in map 200. Perimeter 212 acts as a boundary defining two regions of the map: an internal region 216 within the perimeter, and an external region 220 outside the perimeter. As is explained below, either region may be considered to be a selected region wherein graphic attributes of map elements in the region are altered.

In one embodiment the user may delineate perimeter 212 using pointing device 48. Alternatively, the delineation may be pre-set, for example, by generating a pre-set perimeter around a selected region of map 200 or around an icon of a catheter, such as icon 208 used in the map, or around another point such as a center of mass of the icon. Furthermore, the perimeter may be delineated using a combination of user input, typically using pointing device 48, and pre-set factors such as those exemplified above. Other methods for delineating the perimeter will be apparent to those having ordinary skill in the art, and all such methods are assumed to be comprised within the scope of the present invention.

While perimeter 212 may be any closed regular or irregular figure, in the following description, except where otherwise indicated, for simplicity perimeter 212 is assumed to be a circle, as is illustrated in FIG. 6.

The user may dimension perimeter 212 to have any convenient size, and may position perimeter 212 at substantially any location of map 200. By way of example, perimeter 212 is assumed to be dimensioned and positioned so as to surround icon 208, and so that the icon is approximately at the center of the perimeter.

In addition to delineating perimeter 212, in selection step 104 the user defines how the graphic attributes of map elements, of both property parameters and geometric figures, within the perimeter or outside the perimeter, are to be changed. Such a definition typically changes how the parameters and figures are perceived by the user. The definition may apply to both kinds of entities, or alternatively the definition may apply to one of the entities. The definition may comprise changing color values of map element pixels in a map region, such as by effectively adding a filter to enhance or deemphasize selected colors in the region, changing the transparency or opacity of the region, and/or changing colored objects within the region to be shown in "false" colors, or as grayscale, or as black and white elements. Other graphic attributes that may be defined include the visibility, the brightness, the contrast, the sharpness and/or the softness of the map elements.

For geometric figures, graphic attributes other than those exemplified above may also be defined. For example, for a geometric figure such as icon 208, the size and/or the shape and/or the orientation of the figure may be defined.

In a display step 106, processor 40 changes the display of map 200 in either internal region 216 or external region 220 according to the graphic attribute definitions implemented in step 104. Thus the graphic attributes within one of the regions are unaltered, while the graphic attributes of the other region are altered. The region where graphic attributes are unaltered is herein termed the non-selected region. The region where graphic attributes are altered is herein termed the selected region. In display step 106 the user is typically able to select if the perimeter itself is, or is not, displayed.

In one embodiment the user defines the graphic attributes of property parameters and geometric figures in internal region 216, within perimeter 212, to be unaltered, so that the internal region is the non-selected region. The graphic attributes of parameters and figures outside the perimeter, in external region 220, are altered so that external region 220 is the selected region. The graphic attribute alteration is such that the parameters and figures in the external region are less conspicuous than those of the internal region.

Figure 7:
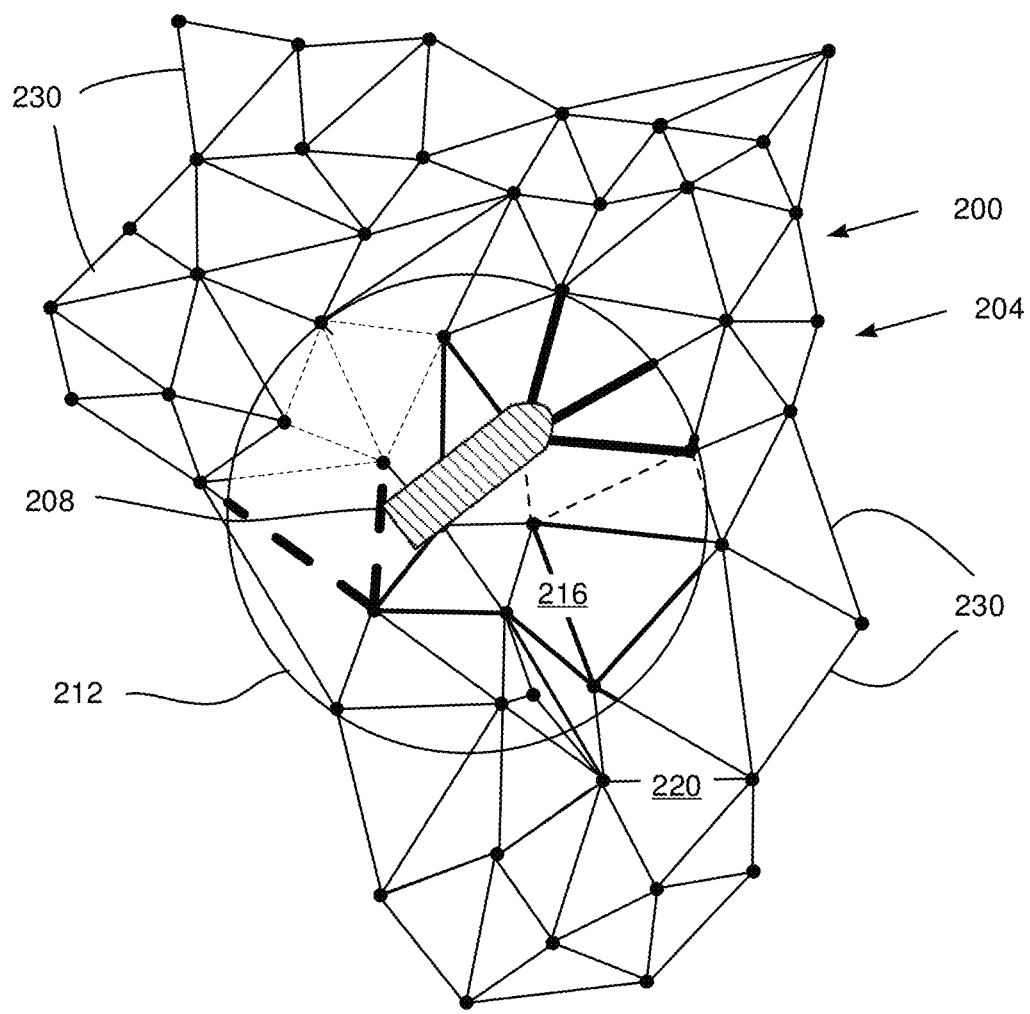
FIG. 7 is a schematic diagram of the mesh map of FIG. 6 illustrating alteration of graphic attributes, according to an embodiment of the present invention.

Such an alteration allows the user to concentrate on parameters and figures within the perimeter, without being distracted by parameters and figures outside the perimeter. FIG. 7 schematically illustrates the display for this case. By way of example, all line elements 230 outside perimeter 212, in selected region 220, have been set to have approximately the same color level value, which could be differing shades of a single color or even the same or differing shades of gray. This is in contrast to line elements within the perimeter, which have color values that are unaltered from the original color values of the map.

Embodiments of the present invention also allow perimeter 212 to be moved and/or resized, while the definitions of the graphic attributes in the external region and in the internal region are unchanged. The movement and/or the resizing may be accomplished using pointing device 48, typically depending upon how the perimeter has been previously delineated, as described above for step 104.

Figure 8:
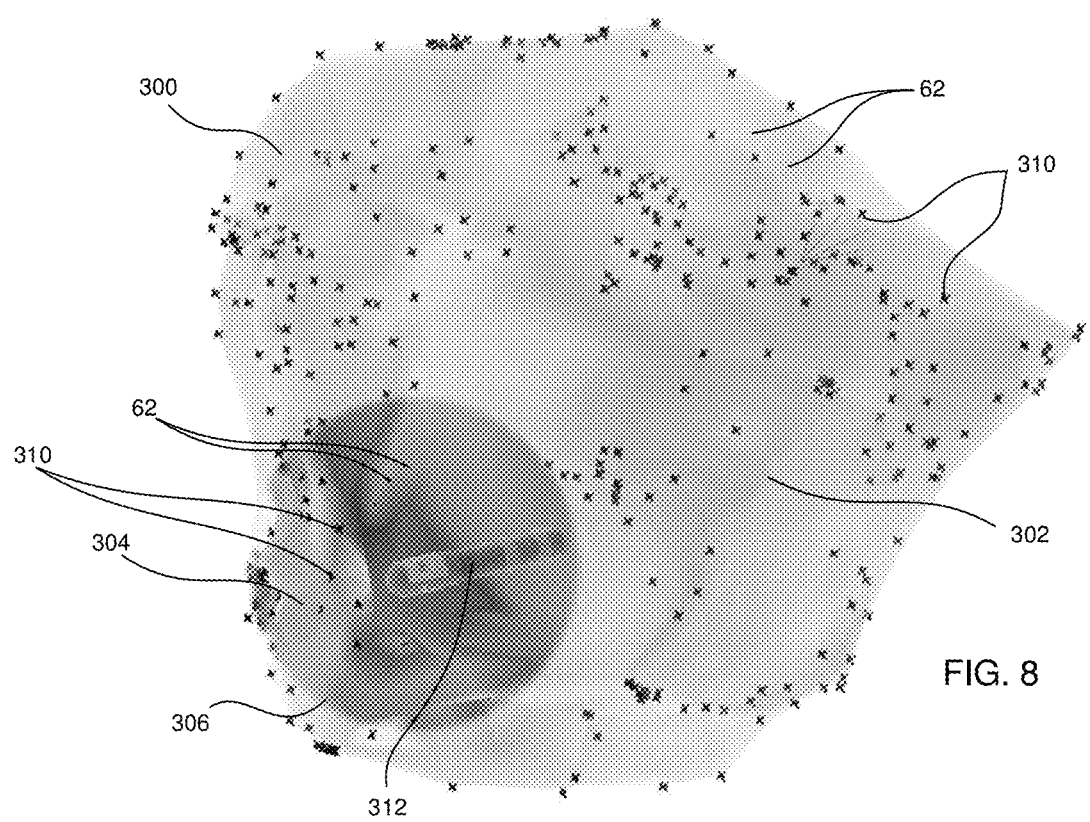
FIG. 8 schematically illustrates a surface map that is displayed in a step of the flowchart of FIG. 2, according to an embodiment of the present invention.
Figure 9:
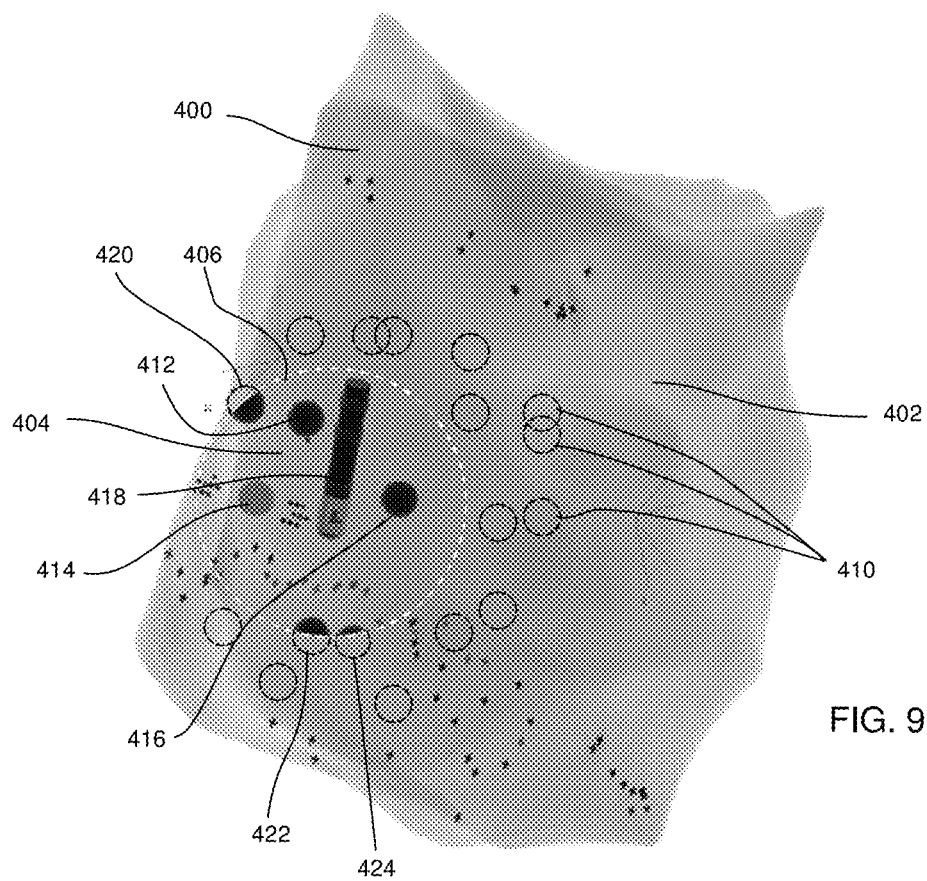
FIG. 9 schematically illustrates an alternative surface map that is displayed in a step of the flowchart of FIG. 2, according to an embodiment of the present invention.

The description above assumes that in initial step 102 of the flowchart a mesh map is selected. FIGS. 8 and 9 are schematic illustrations of the display presented to the user if a surface map is selected in the initial step of the flowchart.

FIG. 8 schematically illustrates a surface map 300 that is displayed in display step 106 of flowchart 100, according to an embodiment of the present invention. Map 300 assumes that a corresponding surface map (not shown in the figures) has been selected in step 102.

In step 102 the property parameters of the selected surface map are assumed to be LATs, and the map is displayed on screen 50 with different colors representing different values of the LATs. Geometric figures illustrating positions where an electropotential has been measured are represent by crosses in the map displayed on the screen in step 102, and a geometric figure representing a catheter distal tip location and orientation is also displayed in the map. In step 102 the property parameters of the selected surface map, i.e., the LATs, and also the geometric figures, have a high contrast, as well as a high brightness throughout the map.

Surface map 300, displayed in step 106, comprises a selected region 302 and a non-selected region 304, the two regions being separated by a perimeter 306 which is defined in step 104 of the flowchart. In selected region 302, outside perimeter 306, graphic attributes of property parameters 62, the LATs, within the region, comprising the contrast within the region and the overall brightness of the region, have been altered from their initial states present in step 102. The alteration is implemented in step 104 and reduces the contrast and the brightness of elements illustrating the property parameters within the region, compared to the contrast and the brightness of the property parameter elements prior to the process of flowchart 100 being applied. However, in step 104 graphic attributes within non-selected region 304, comprising the contrast and brightness of the elements representing property parameters 62 in the non-selected region, are unaltered from the high contrast and brightness values present in the region in step 102.

In addition, in step 104, there is no alteration of the display of geometric FIG. 64, herein assumed to comprise crosses 310 and icon 312. Thus crosses 310 are displayed as substantially similar crosses in both selected region 302 and non-selected region 304.

FIG. 9 schematically illustrates a surface map 400 that is displayed in display step 106 of flowchart 100, according to an embodiment of the present invention. Map 400 assumes that a corresponding surface map (not shown in the figures) has been selected in step 102.

In step 102 the property parameters of the selected surface map are assumed to be LATs, and the map is displayed on screen 50 with different colors representing different values of the LATs. The geometric figures are represented by circular icons in the map displayed on the screen in step 102, and illustrate positions where an ablation has been performed. The circular ablation icons are colored differently to represent a property of the ablation, such as an overall energy used in performing the ablation. In addition, another geometric figure, a distal tip icon, is present in the map displayed in step 102.

Surface map 400, displayed in step 106, comprises a selected region 402 and a non-selected region 404, the two regions being separated by a perimeter 406 which is defined in step 104 of the flowchart. In selected region 402, outside perimeter 406, graphic attributes of geometric figures within the region, which in this case include icons 410 representing ablation locations and properties, have been altered from their initial states present in step 102. The alteration is implemented in step 104 and renders icons 410 invisible in the selected region. In the figure, locations of invisible icons 410 are illustrated by broken circles. However, in step 104 graphic attributes of geometric figures within non-selected region 404, comprising circular ablation icons 412, 414, and 416 and a distal tip icon 418, are unaltered from their values present in the region in step 102. As illustrated in FIG. 9, icons 412 and 416 have the same color, which is different from the color of icon 414.

Icons 420, 422, and 424 are examples of icons that are partially altered from their initial values, by being cut by perimeter 406. Thus, in region 402, the portions of icons 420, 422, and 424 outside the perimeter are rendered invisible. Within the perimeter, the portions of icons 420, 422, and 424 are unaltered.

The embodiments described above illustrate examples of how a 3D map may be divided into two regions, and the graphic attribute of map elements within one of the regions are altered. As a further example, referring back to the mesh map illustrated in FIGS. 5, 6, and 7, a graphic attribute of the selected region may be altered to display the selected region as a surface, rather than the mesh that continues to be displayed in the non-selected region. The graphic attribute of the non-selected region defines the region as a mesh.

As another example, again referring to the mesh maps of FIGS. 5-7 which display LAT values, the graphic attribute of the selected region may be altered to illustrate the LATs as unipolar values, while the graphic attribute of the non-selected region continues to illustrate the LATs as bipolar values. Other examples of alteration of the graphic attribute of map elements in a selected region of a 3D map will be apparent to those having ordinary skill in the art, and all such examples are assumed to be within the scope of the present invention.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for mapping a body organ, comprising:
   receiving a selection of a three-dimensional (3D) map of the body organ to be displayed;
   receiving a selection of a multiplicity of map elements to be incorporated into the 3D map, each map element having a graphic attribute indicative of a local property of the body organ;
   delineating a selected region of the map, so that the map is divided into the selected region and a non-selected region; and
   displaying the 3D map incorporating the selection of the multiplicity of map elements while altering the graphic attribute of the map elements specifically within the selected region.

2. The method according to claim 1, wherein displaying the 3D map comprises not altering the graphic attribute of the geometric map-elements within the non-selected region.

3. The method according to claim 1, wherein delineating the selected region comprises generating a closed perimeter on the 3D map separating the selected region from the non-selected region.

4. The method according to claim 3, wherein the selected region is within the perimeter.

5. The method according to claim 3, wherein the selected region is external to the perimeter.

6. The method according to claim 1, wherein delineating the selected region comprises initially generating a closed perimeter on the 3D map separating the selected region from the non-selected region, and subsequently changing the closed perimeter so as to alter the selected region and the non-selected region.

7. The method according to claim 1, wherein the body organ comprises a heart, and wherein the local property comprises at least one of a temperature, an electropotential, a resistivity, a contractility, and a local activation time (LAT) of the heart.

8. The method according to claim 1, and comprising:
   incorporating into the 3D map one or more geometric figures, each geometric figure being representative of at least a portion of an entity associated with a local region of the body organ and having a further graphic attribute, and
   displaying the 3D map while altering the further graphic attribute of the one or more geometric figures specifically within the selected region.

9. The method according to claim 1, wherein the graphic attribute comprises at least one of a color value, a visibility, and a transparency.

10. A method for mapping a body organ, comprising:
    receiving a selection of a three-dimensional (3D) map of the body organ to be displayed;
    receiving a selection of one or more geometric figures, each geometric figure having a graphic attribute and being representative of at least a portion of an entity associated with a local region of the body organ;
    delineating a selected region of the map, so that the map is divided into the selected region and a non-selected region; and
    displaying the 3D map incorporating the selection of one or more geometric figures while altering the graphic attribute of each geometric figure specifically within the selected region.

11. The method according to claim 10, wherein the geometric figures comprise at least one of a distal tip icon representative of a location and orientation of a catheter distal tip and an ablation icon representative of an ablation performed on a region of the body organ.

12. Apparatus for mapping a body organ, comprising:
    a processor which is configured to:
      receive a selection of a three-dimensional (3D) map of the body organ to be displayed;
      receive a selection of a multiplicity of map elements, each map element having a graphic attribute indicative of a local property of the body organ;
      and delineate a selected region of the map, so that the map is divided into the selected region and a non-selected region; and
    a screen which is configured to display the 3D map incorporating of the selection of the multiplicity of map elements while altering the graphic attribute of the map elements specifically within the selected region.

13. The apparatus according to claim 12, wherein displaying the 3D map comprises not altering the graphic attribute of the geometric map-elements within the non-selected region.

14. The apparatus according to claim 12, wherein delineating the selected region comprises generating a closed perimeter on the 3D map separating the selected region from the non-selected region.

15. The apparatus according to claim 14, wherein the selected region is within the perimeter.

16. The apparatus according to claim 14, wherein the selected region is external to the perimeter.

17. The apparatus according to claim 12, wherein delineating the selected region comprises initially generating a closed perimeter on the 3D map separating the selected region from the non-selected region, and subsequently changing the closed perimeter so as to alter the selected region and the non-selected region.

18. The apparatus according to claim 12, wherein the body organ comprises a heart, and wherein the local property comprises at least one of a temperature, an electropotential, a resistivity, a contractility, and a local activation time (LAT) of the heart.

19. The apparatus according to claim 12, wherein the processor is configured to incorporate into the 3D map one or more geometric figures, each geometric figure being representative of at least a portion of an entity associated with a local region of the body organ and having a further graphic attribute, and wherein the screen is configured to display the 3D map while altering the further graphic attribute of the one or more geometric figures specifically within the selected region.

20. The apparatus according to claim 12, wherein the graphic attribute comprises at least one of a color value, a visibility, and a transparency.

21. Apparatus for mapping a body organ, comprising:
a processor which is configured to:
receive a selection of a three-dimensional (3D) map of the body organ to be displayed;
receive a selection of one or more geometric figures, each geometric figure having a graphic attribute and being representative of at least a portion of an entity associated with a local region of the body organ; and
delineate a selected region of the map, so that the map is divided into the selected region and a non-selected region; and
a screen which is configured to display the 3D map incorporating the selection of one or more geometric figures while altering the graphic attribute of the each geometric figure specifically within the selected region.

22. The apparatus according to claim 21, wherein the geometric figures comprise at least one of a distal tip icon representative of a location and orientation of a catheter distal tip and an ablation icon representative of an ablation performed on a region of the body organ.

* * * * *